United States Patent [19]
Bessler et al.

[11] Patent Number: 5,855,601
[45] Date of Patent: Jan. 5, 1999

[54] ARTIFICIAL HEART VALVE AND METHOD AND DEVICE FOR IMPLANTING THE SAME

[75] Inventors: Marc Bessler, Teaneck, N.J.; Timothy A. M. Chuter, Malmö, Sweden

[73] Assignee: The Trustees of Columbia University in the City of New York, New York, N.Y.

[21] Appl. No.: 668,376

[22] Filed: Jun. 21, 1996

[51] Int. Cl.⁶ .................................................. A61F 2/24
[52] U.S. Cl. .............................................. 623/2; 623/900
[58] Field of Search .................................. 623/2, 1, 900

[56] References Cited

U.S. PATENT DOCUMENTS

| | | |
|---|---|---|
| 3,574,865 | 4/1971 | Hamaker ................................ 623/2 |
| 3,671,979 | 6/1972 | Moulopoulos . |
| 3,874,388 | 4/1975 | King et al. . |
| 4,056,854 | 11/1977 | Boretos et al. . |
| 4,592,340 | 6/1986 | Boyles . |
| 4,631,052 | 12/1986 | Kensey . |
| 4,692,139 | 9/1987 | Stiles . |
| 4,705,507 | 11/1987 | Boyles . |
| 4,794,928 | 1/1989 | Kletschka . |
| 4,816,029 | 3/1989 | Penny, III et al. ..................... 623/2 |
| 4,883,458 | 11/1989 | Shiber . |
| 4,886,061 | 12/1989 | Fischell et al. . |
| 4,960,424 | 10/1990 | Grooters . |
| 4,966,604 | 10/1990 | Reiss . |
| 4,979,939 | 12/1990 | Shiber . |
| 4,994,077 | 2/1991 | Dobben . |
| 5,007,896 | 4/1991 | Shiber . |
| 5,019,090 | 5/1991 | Pinchuk . |
| 5,032,128 | 7/1991 | Alonso . |
| 5,047,041 | 9/1991 | Samuels . |
| 5,069,679 | 12/1991 | Taheri . |
| 5,080,660 | 1/1992 | Buelna . |
| 5,133,725 | 7/1992 | Quadri . |
| 5,141,491 | 8/1992 | Bowald . |
| 5,152,771 | 10/1992 | Sabbaghian et al. . |
| 5,163,953 | 11/1992 | Vince . |
| 5,297,564 | 3/1994 | Love . |
| 5,332,402 | 7/1994 | Teitelbaum . |
| 5,370,685 | 12/1994 | Stevens . |
| 5,397,351 | 3/1995 | Pavcnik et al. ........................... 623/2 |
| 5,411,552 | 5/1995 | Andersen et al. ........................ 623/2 |
| 5,469,868 | 11/1995 | Reger . |
| 5,480,424 | 1/1996 | Cox . |
| 5,489,295 | 2/1996 | Piplani et al. ............................ 623/1 |
| 5,489,298 | 2/1996 | Love et al. . |
| 5,562,729 | 10/1996 | Purdy et al. .............................. 623/2 |
| 5,571,175 | 11/1996 | Vanney et al. ........................... 623/2 |

FOREIGN PATENT DOCUMENTS

| | | |
|---|---|---|
| 1644946A | 4/1991 | Russian Federation . |
| 1697790 | 12/1991 | U.S.S.R. .................................. 623/2 |
| WO 91/17118 | 11/1991 | WIPO . |
| WO 91/17720 | 11/1991 | WIPO . |
| 9407437 | 4/1994 | WIPO ..................................... 623/2 |

*Primary Examiner*—Michael J. Milano
*Assistant Examiner*—Tram A. Nguyen
*Attorney, Agent, or Firm*—Cowan, Liebowitz & Latman, P.C.; William H. Dippert

[57] ABSTRACT

An artificial heart valve comprises a relatively rigid stent member having a first cylindrical shape and a flexible valve disposed in the stent member, the stent member being self-expandable to a second cylindrical shape and collapsible to its first cylindrical shape. The valve comprises a circular portion comprising a plurality of leaflets extending from the periphery of the circular portion towards the center thereof, the leaflets being configured to allow for flow of blood through the valve in one direction only. The diameter of the circular portion is substantially the same as the inside diameter of the stent member when the stent member is in its second cylindrical shape, the valve member being attached to the stent member.

20 Claims, 8 Drawing Sheets

ARTIFICIAL HEART VALVE AND METHOD AND DEVICE FOR IMPLANTING THE SAME

FIELD OF THE INVENTION

The present invention relates to novel artificial heart valves. More particularly, the present invention relates to novel heart valves that are especially adapted for placement using minimally invasive surgical techniques and to the method and device useful for such placement.

BACKGROUND OF THE INVENTION

Over the past several years a number of less invasive or minimally invasive surgical techniques have been developed. Examples of such techniques are various endoscopic or laparoscopic procedures, angioplasty procedures, atherectomy procedures, and the like. While the instruments and devices used in these minimally invasive procedures are complex and hence relatively expensive, the procedures are gaining more and more acceptance. It is believed the reasons for this acceptance are the reduced risk to the patient, as the patient often doesn't have to undergo general anesthesia or the time under general anesthesia is greatly reduced. Perhaps, more importantly, the recovery time required after a minimally invasive procedure is much less, thus greatly reducing hospital costs.

One of the more invasive procedures being performed today is open heart surgery. Such procedures require the use of general anesthesia, sternotomy, use of extracoporeal by-pass, recovery in an intensive care unit, and a stay of at least a few days in the hospital. Although such procedures carry a low mortality rate, they are quite expensive.

Currently in the United States approximately 100,000 defective heart valves are replaced annually, at an approximate cost of $30–50,000 per procedure, and thus it would be desirable if heart valves could be replaced using minimally invasive techniques. It would be especially advantageous if a defective heart valve could be removed via an endovascular procedure, that is, a procedure where the invasion into the body is through a blood vessel such as the femoral artery. The procedure is then carried out percutaneously and transluminally using the vascular system to convey appropriate devices to the position in the body wherein it is desired to carry out the desired procedure. An example of such a procedure would be angioplasty, wherein a catheter carrying a small balloon at its distal end is manipulated through the body's vessels to a point where there is a blockage in a vessel. The balloon is expanded to create an opening in the blockage, and then the balloon is deflated and the catheter and balloon are removed from the vessel.

Endovascular procedures have substantial benefits both from the standpoint of health and safety as well as cost. Such procedures require minimal invasion of the human body, and there is consequently considerable reduction and in some instances even elimination, of the use of a general anesthesia and much shorter hospital stays.

In the last few years a number of atherectomy devices have been developed. These are endovascular devices used to remove plaque and other abnormal deposits from vessels. Representative examples of such devices are those disclosed in U.S. Pat. Nos. 4,445,509, 4,646,736, and 4,990,134.

A number of minimally invasive techniques for replacing heart valves have been developed. Such techniques have been reported in an article by H. R. Andersen et al., entitled "Transluminal Implantation of Artificial Heart Valves", *European Heart Journal* (1992), Vol. 13, pp. 704–708; in an article by L. L. Knudsen et al., entitled "Catheter-Implanted Prosthetic Heart Valves", *The International Journal of Artificial Organs,* Vol. 16, No. 5 (1993), pp. 253–262; and in an article by D. Pavcnik et al., entitled "Development and Initial Experimental Evaluation of a Prosthetic Aortic Valve for Trans-Catheter Placement", *Radiology* (1992), Vol. 183, pp. 151–154. While the devices and techniques reported are clearly experimental, it appears that each of them suffers from one or more of the following problems: (1) secure placement of the heart valve; (2) durability of the heart valve; (3) ease of placement; (4) thrombogenicity, (5) leakage or regurgitation of blood, (6) excessive pressure gradient across the valve, and (7) size of the device and delivery system, as well as other similar problems. In addition, none of the above described devices or methods deals with the presence of a diseased or defective native valve.

An endovascular valve replacement procedure is described in Stevens, U.S. Pat. No. 5,370,685. While it cannot be discerned whether the procedure disclosed will work, it is evident that the replacement valve is structurally limited and will have the disadvantages associated with the problems discussed above.

OBJECTS OF THE INVENTION

It is an object of the present invention to provide endovascular procedures and devices for the percutaneous and transluminal replacement of diseased or defective heart valves.

It is also an object of the present invention to provide a heart valve that can be relatively easily placed and secured in position.

It is a further object of the present invention to provide a valve that is relatively non-thrombogenic and eliminates undesirable leakage.

It is a still further object of the present invention to provide a method and device for the simple placement and securement of the new and improved heart valve in the desired position in a patient.

It is likewise an object of the present invention to provide a method and device for implanting an artificial heart valve using minimally invasive techniques especially endovascular techniques.

It is an even further object of the present invention to provide a method and device for the percutaneous and transluminal removal of a defective heart valve.

It is additionally a further object of the present invention to provide for the minimally invasive or endovascular placement of heart valves while preventing embolization.

These and other objects of the invention will become more apparent in the discussion below.

SUMMARY OF THE INVENTION

The invention herein encompasses methods and devices for the endovascular removal and replacement of diseased or defective heart valves. The invention includes a new heart valve which may be implanted percutaneously and transluminally, which heart valve comprises a stent member and a valve means. The stent member is self-expanding and has within it valve means that permit flow in only one direction. Preferably the stent member has barbs which anchor the expanded stent member at a desired site. A cutting mechanism is used to remove the diseased or defective heart valve, and then the replacement valve is inserted percutaneously to the site, where it is released in a controlled fashion from the distal end of a catheter.

DETAILED DESCRIPTION OF THE INVENTION

The present invention includes methods and devices for implanting a heart valve percutaneously and transluminally. The artificial heart valves of the invention, which are capable of exhibiting a variable diameter between a compressed or collapsed position and an expanded position, comprise (1) a relatively rigid stent member and (2) a flexible valve means. The stent member is self-expanding and has a first cylindrical shape in its compressed or collapsed configuration and a second, larger cylindrical shape in its expanded configuration. The flexible valve means comprises a generally arcuate center portion and, preferably, a peripheral upstanding cuff portion. The flexible valve means is disposed within the cylindrical stent member with the arcuate portion transverse of and at some acute angle relative to the stent walls. The diameter of the arcuate portion is substantially the same as the inside diameter of the stent member in its initial expanded configuration. The peripheral upstanding cuff portion is disposed substantially parallel to the walls of the stent member.

The arcuate portion of the valve means contains at least one slit to form leaflets which open in response to blood flow in one direction and close in response to blood flow in the opposite direction. Preferably the arcuate portion of the valve means contains a plurality of leaflets and most preferably three leaflets.

The cuff portion of the valve means is attached to the stent member and may extend partly or wholly around the outer perimeter of the stent member. In some of the preferred embodiments of the artificial heart valve of the invention, the cuff portion of the valve means extends on only one side of the circular portion of the stent member. The flexible valve means preferably comprises porcine pericardium configured with three leaflets.

Preferably the stent member carries a plurality of barbs extending outwardly from the outside surface of the stent member for fixing the heart valve in a desired position. More preferably the barbs are disposed in two spaced-apart, circular configurations with the barbs in one circle extending in an upstream direction and the barbs in the other circle extending in a downstream direction. It is especially preferable that the barbs on the inflow side of the valve point in the direction of flow and the barbs on the outflow side point in the direction opposite to flow. It is preferred that the stent be formed of titanium alloy wire or other flexible, relatively rigid, physiologically acceptable material arranged in a closed zig-zag configuration. Such a configured stent member will readily collapse and expand as pressure is applied and released, respectively.

The invention includes methods and devices for the percutaneous and transluminal removal of the diseased or defective heart valve and the percutaneous and transluminal implantation of the new heart valve described above. The defective heart valve is removed by a suitable modality, such as, for example, laser, ultrasound, mechanical, or other suitable forms of delivery of energy, or phacoemulsion, including, but not limited to, laser lithotripsy, mechanical lithotripsy, electrohydraulic lithotripsy, and laser or mechanical ablation. For example, the valve can be ground or cut into fine particles or pieces and the particles are gathered and removed. The device for grinding or cutting the defective heart valve and removing the debris can include a rotating cutting tool mounted on the end of a flexible drive shaft. The drive shaft is surrounded over most of its length by a guiding catheter. The cutting tool, which is inserted into a vessel of the patient and guided to the location of the defective heart valve, may comprise cutting blades disposed at its distal end. The blades are configured such that the debris that is created by the cutting action is thrown or ejected proximal of the distal end. Disposed close to the cutting blades and proximal thereof is a collecting member which preferably has a concave shape and is expandable to occlude the aorta as well as to catch debris. If desired the collecting member may be perforated so that suction may be used to aid in the removal of the ground debris.

The system for implanting the above described artificial heart valve percutaneously and transluminally includes a flexible catheter which may be inserted into a vessel of the patient and moved within that vessel. The distal end of the catheter, which is hollow and carries the artificial heart valve of the present invention in its collapsed configuration, is guided to a site where it is desired to implant the artificial heart valve. The catheter has a pusher member disposed within the catheter lumen and extending from the proximal end of the catheter to the hollow section at the distal end of the catheter. Once the distal end of the catheter is positioned as desired, the pusher mechanism is activated and the distal portion of the artificial heart valve is pushed out of the catheter and the stent member partially expands. In this position the stent member is restrained so that it doesn't pop out and is held for controlled release, with the potential that the artificial heart valve can be recovered if there is a problem with the positioning or the like. The catheter is them retracted slightly and the artificial heart valve is completely pushed out of the catheter and released from the catheter to allow the stent member to fully expand. If the stent member includes two circles of barbs on its outer surface as previously described, the first push and retraction will set one circle of barbs in adjacent tissue and the second push and release of the artificial heart valve will set the other circle of barbs in adjacent tissue and securely fix the artificial heart valve in place when the valve is released from the catheter. Alternatively, or in combination with the above, the heart valve could be positioned over a guidewire.

Figure 1:
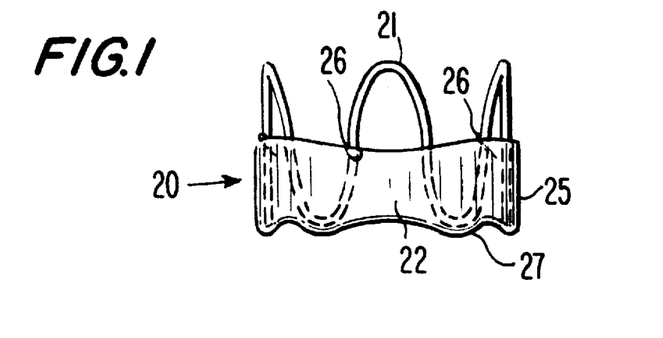
FIG. 1 is a front, partially cross-sectional view of an artificial heart valve of the present invention.
Figure 2:
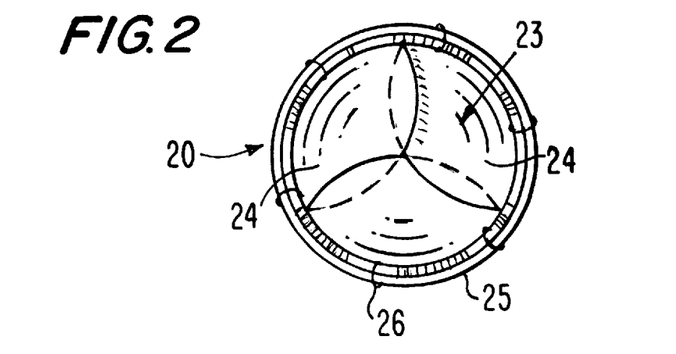
FIG. 2 is a top view of the artificial heart valve depicted in FIG. 1.
Figure 3:
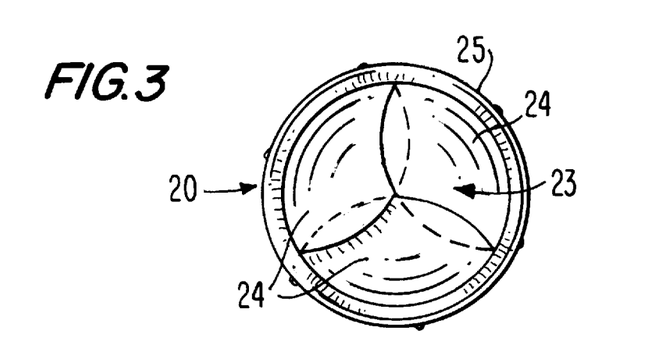
FIG. 3 is a bottom view of the artificial heart valve depicted in FIG. 1.

The invention can perhaps be better appreciated by reference to the drawings. An artificial heart valve according to the present invention is set forth in FIGS. 1 to 3. The artificial heart valve 20 is comprised of a stent member 21 and a flexible valve means 22. In this embodiment the stent member 21 is comprised of stainless steel wire in a sine wave-like configuration as shown in FIG. 1. The center portion 23 of valve member 22 is generally arcuate in shape and comprises three leaflets 24 as shown, although it is understood that there could be from 2 to 4 leaflets. A cuff portion 25 extends from the periphery of the circular portion 27 along the outside of the stent member 21 and is attached to the stent member 21 by a plurality of sutures 26.

Figure 4:
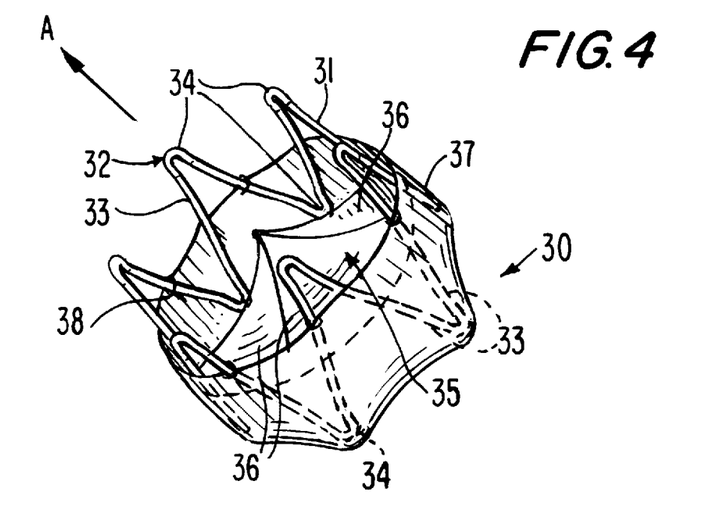
FIG. 4 is a perspective, partially cross-sectional view of an artificial heart valve of the invention in an expanded configuration.

FIG. 4 is a perspective view of another embodiment of an artificial heart valve 30 of the invention. The heart valve 30 has a generally circular shape with the walls 31 of the cylinder being formed by the stent member 32. The stent member 32 is a wire formed in a closed zig-zag configuration. The member has an endless series of straight sections 33 joined by bends 34. The valve member 35 is flexible and includes a plurality of leaflets 36.

The leaflet portion of the valve member 35 extends across or transverse of the cylindrical stent. The leaflets 36 are the actual valve and allow for one-way flow of blood. Extending from the periphery of the leaflet portion is a cuff portion 37. The cuff portion 37 extends adjacent the stent walls 31 in the direction of the arrow A. The cuff portion is attached to the stent by sutures 38.

Figure 5:
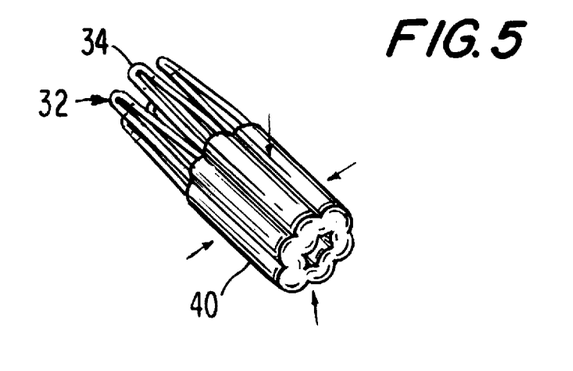
FIG. 5 is a perspective view of an artificial heart valve of the invention in a collapsed or constrained configuration.

The configuration of the stent member 32 and the flexible, resilient material of construction allows the valve to collapse into a relatively small cylinder 40 as seen in FIG. 5. The artificial heart valve will not stay in its collapsed configuration without being restrained. Once the restraint is removed, the self-expanding stent member 32 will cause the artificial heart valve to take its expanded configuration, as seen in FIG. 4.

Figure 6:
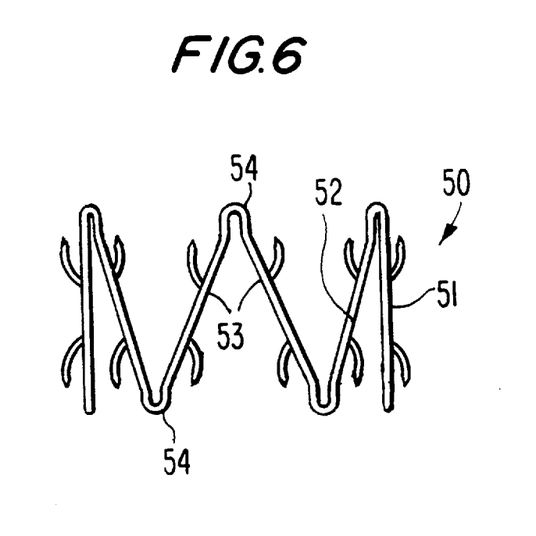
FIG. 6 is an expanded front view of a segment of one type of stent member that may be used in the artificial heart valves of the invention.

An enlarged view of a preferred embodiment of a stent member for use in the artificial heart valve of the invention is depicted in FIG. 6. The stent member 50 includes a length of wire 51 formed in a closed zig-zag configuration. The wire can be a single piece, stamped or extruded, or it could be formed by welding the free ends together as at 52. The straight sections 53 of the stent are joined by bends 54. The stent is readily compressible to a small cylindrical shape and resiliently self-expandable to the shape shown in FIG. 6.

Figure 7:
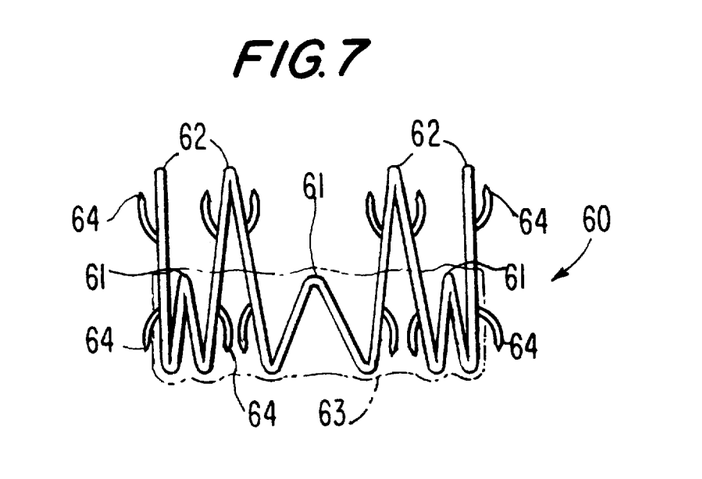
FIG. 7 is a front, partially cross-sectional view of another embodiment of an artificial heart valve of the invention.

Another embodiment of the artificial heart valve of the present invention is depicted in FIG. 7. In this embodiment the heart valve 60 has a modified sine wave configuration. As seen in the drawing every other wave 61 has approximately 0.50–0.75 the amplitude of adjacent waves 62. The flexible valve member 63 is disposed at the crown or top of the smaller waves. The larger waves carry a plurality of barbs 64 for holding the valve in place once it has been appropriately positioned.

The stent members of the artificial heart valves of the present invention may be made from Elgiloy alloy, titanium, titanium alloy, nitinol, stainless steel, or other resilient, flexible non-toxic, non-thrombogenic, physiologically acceptable and biocompatible materials. The configuration may be the zig-zag configuration shown or a sine wave configuration, mesh configuration or a similar configuration which will allow the stent to be readily collapsible and self-expandable. When a zig-zag or sine wave configured stent member is used, the diameter of the wire from which the stent is made should be from about 0.010 to 0.035 inches, preferably from about 0.012 to 0.025 inches. The diameter of the stent member will be from about 1.5 to 3.5 cm, preferably from about 1.75 to 3.00 cm, and the length of the stent member will be from about 1.0 to 10 cm, preferably from about 1.1 to 5 cm.

The valve member is flexible, compressible, host-compatible, and non-thrombogenic. The valve can be, for example, a glutaraldehyde fixed porcine aortic valve which has three cusps that open distally to permit unidirectional blood flow. The valve can also be fresh, cryopreserved or glutaraldehyde fixed allografts or xenografts. The optimal material will be synthetic such that it is manufactured from non-biological materials, non-thrombogenic, flexible such that it can be transported through the vasculature, biocompatible and very durable such that it can withstand a permanent fixation at the valve site. Biocompatible materials such as polytetrafluoroethylene, polyester and the like may be used.

Figure 8:
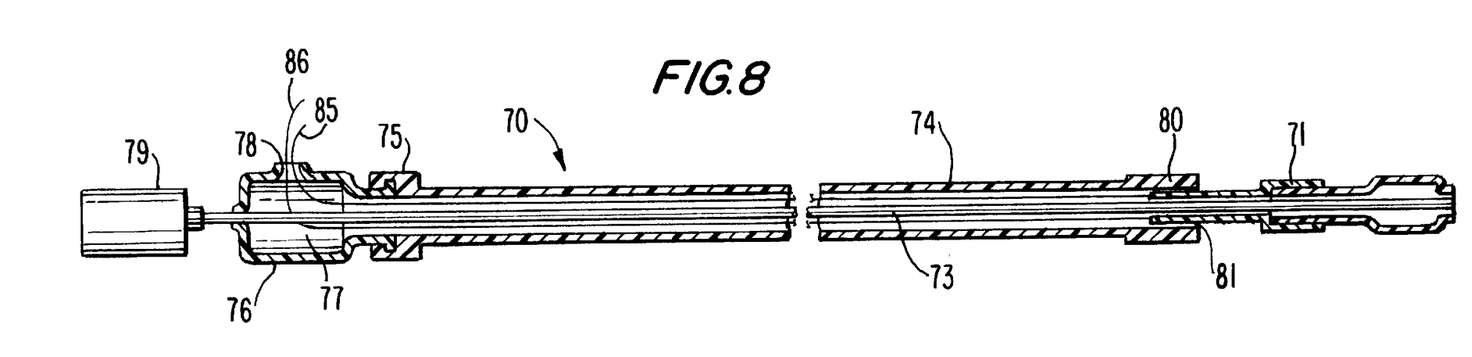
FIG. 8 is a partially cross-sectional view of a device according to the invention for removing a defective or diseased heart valve.
Figure 9:
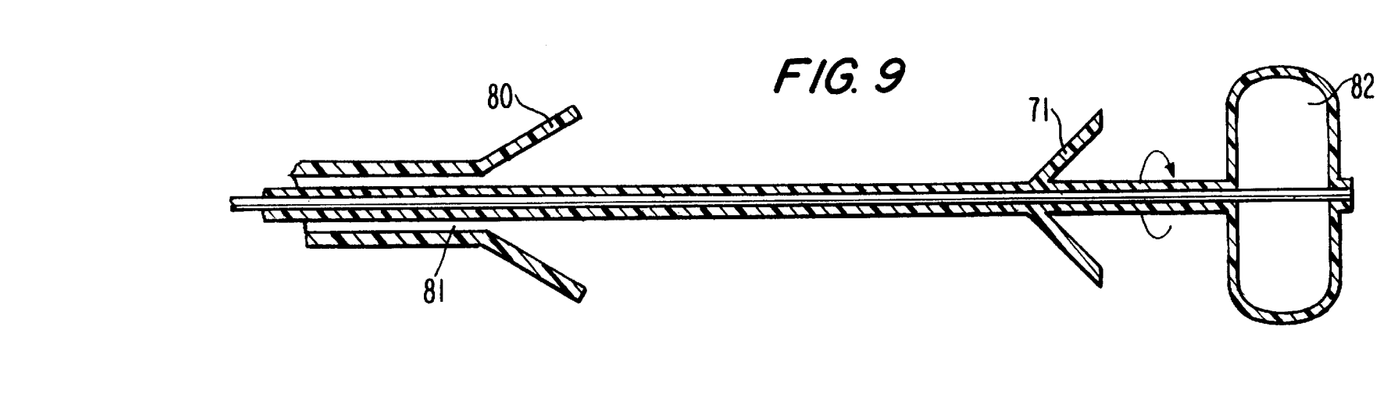
FIG. 9 is an enlarged, cross-sectional view of the distal end of the device shown in FIG. 8.
Figure 10:
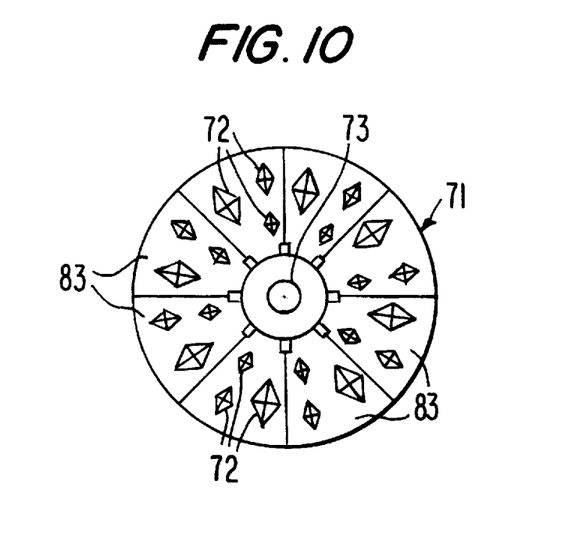
FIG. 10 is a view taken along line 10—10 of FIG. 9.
Figure 11:
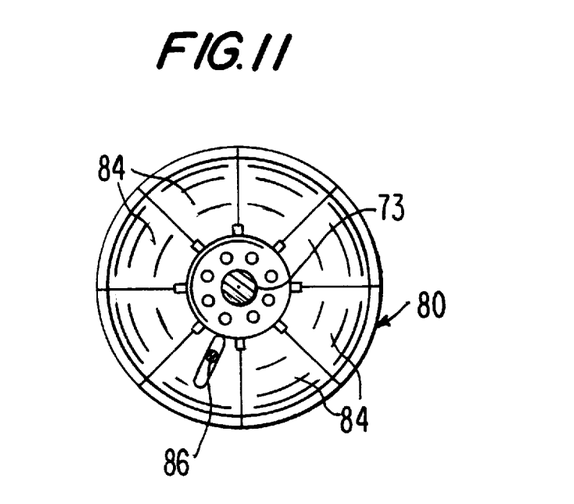
FIG. 11 is a view taken along line 11—11 of FIG. 9.

In FIGS. 8 through 11 there is shown a device for the percutaneous and transluminal removal of a diseased or defective heart valve. The device 70 includes a cutting tool 71 disposed at the distal end of the device 70. As shown in FIG. 10 cutting tool 71 has a plurality of abrasive surfaces 72 on its outer surface for cutting or grinding away the defective heart valve. Abrasive surfaces 72 comprise diamond chips, small metal blades, or other similar abrading means that would be effective to safely remove the defective heart valve. The cutting tool 71 is rotated by a flexible transluminal drive shaft 73, which is preferably contained along substantially its entire length in a flexible catheter 74 made of physiologically acceptable plastic material. At the proximal end of the catheter 74 remote from the cutting tool 71 there is a catheter connector 75 to connect the catheter 74 to a drive shaft bearing block 76. The bearing block includes a central cavity 77 and a port 78. The proximal end of the drive shaft 73 is connected to and through a prime mover or motor 79 for rotation of drive shaft 73 and cutting tool 71.

As is more clearly shown in FIG. 9, disposed just proximal of the cutting tool 71 is a collecting member 80 for collecting debris generated by the cutting or grinding away of the defective heart valve. The collecting member is circular, preferably with a concave shape for directing debris toward the annular space 81 between drive shaft 73 and catheter 74. Suction may be applied to the port 78 in bearing block 76 to assist in removal of debris from the operative site. Collecting member 80 preferably expands due to an inflatable component to cause the outward radial portion of collecting member 80 to abut the inner surface of the appropriate vessel. Thus, all or part of collecting member 80 could be inflatable either in a single inflatable member or a series of inflatable members. Catheter 74 would contain one or more inflation lumens, not shown, in fluid communication with the one or more parts of collecting member 80 to be inflated.

It is preferred that the cutting tool 71 have an initial, relatively small diameter configuration and then a larger configuration as drive shaft 73 and cutting tool 71 are rotated. Alternatively, cutting tool 71 could be mechanically connected to a mechanical rod extending to the proximal end of catheter 74 to cause cutting tool 71 to expand prior to contact with the defective heart valve.

Suction may be applied to the port 78 in the bearing block 76 to assist in the removal of debris from the operative site. Distal protective balloon 82 which is inflated through a lumen in catheter 86 within drive shaft 73, is inflated to a diameter slightly larger than the extended diameter of cutting tool 71.

It is preferred that both the cutting tool 71 and the collecting member 80 be expandable. In the embodiment shown the cutting tool 71 comprises a plurality of leaves 83 and the collecting member basin 80 also comprises a plurality of leaves 84. In both instances the leaves may be mechanically contracted so as to overlap adjacent leaves and reduce the diameter of the respective unit. This will allow both units to be collapsed while being inserted in the vessel and guided to the operative site. The cutting 71 tool is then rotated at a relatively high speed of 3000 to 4000 rpm to grind away the defective valve. The resultant debris is collected in the collecting member 80 and removed from the site with the aid of suction.

Figure 12:
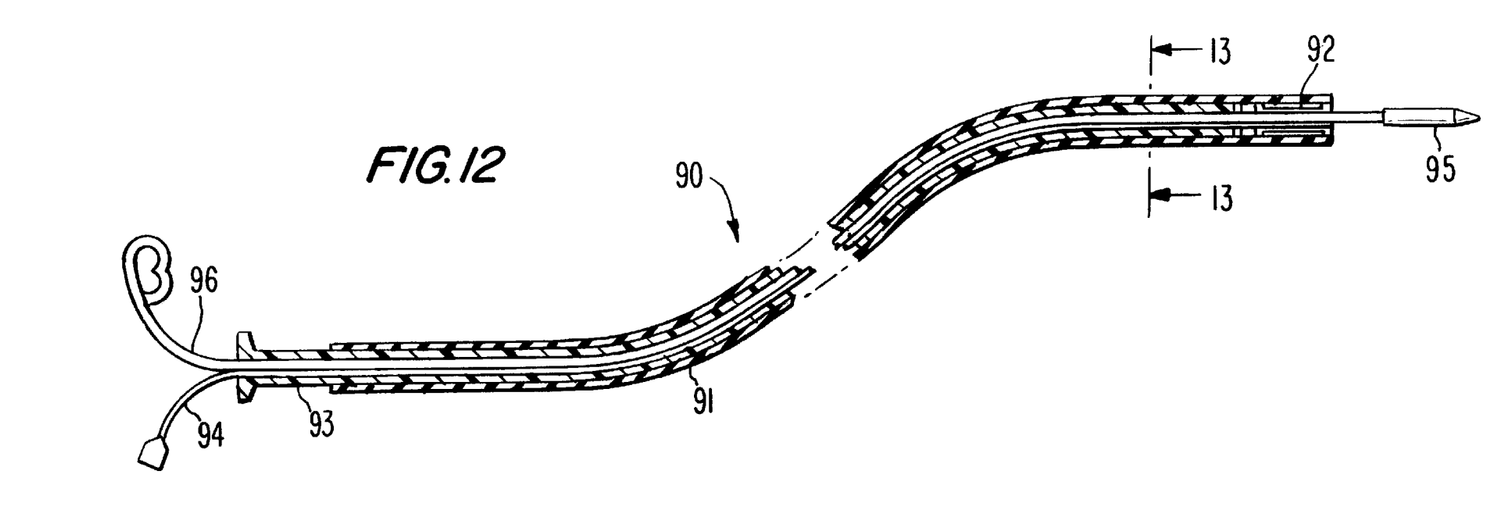
FIG. 12 is a cross-sectional view of a device of the invention for the percutaneous and transluminal implantation of a heart valve.
Figure 13:
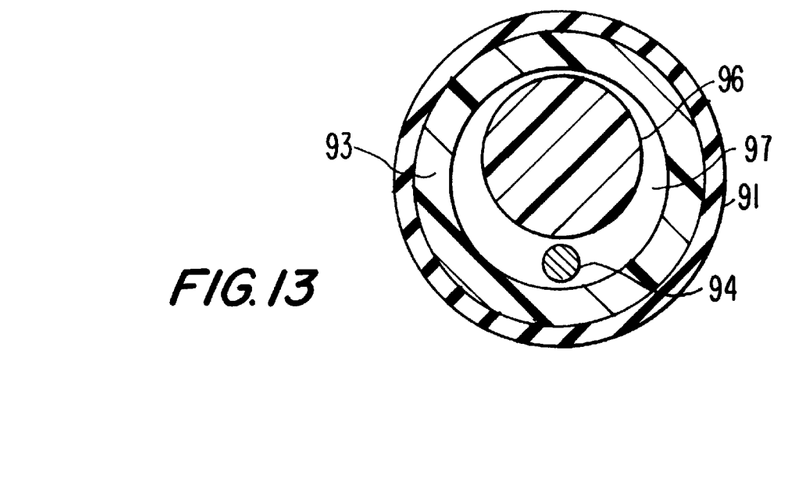
FIG. 13 is an enlarged, cross-sectional view taken along line 13—13 of FIG. 12.

The device set forth in FIGS. 12 and 13 represents a novel device for implanting the artificial heart valves of the present invention. The device 90 comprises a flexible catheter 91 for percutaneous and transluminal delivery of the heart valve to the desired site. A heart valve 92 of the invention is carried, in its collapsed state, at the distal end of the catheter 91 where the catheter walls maintain the valve 92 in its collapsed state. Disposed within the catheter 91 is a hollow flexible pusher member 93, which is movable longitudinally with respect to the catheter 91. A guidewire 94 having a blunt end 95 is disposed through a lumen 97 of the pusher member 93 and is used to guide the distal end of the catheter 91 to the desired site. Means 96 is also disposed through lumen 97 of the pusher member 93 for holding the valve 92 in place and allowing release of the valve 92 when desired, as will be more fully described in conjunction with FIGS. 14 and 15.

Figure 14:
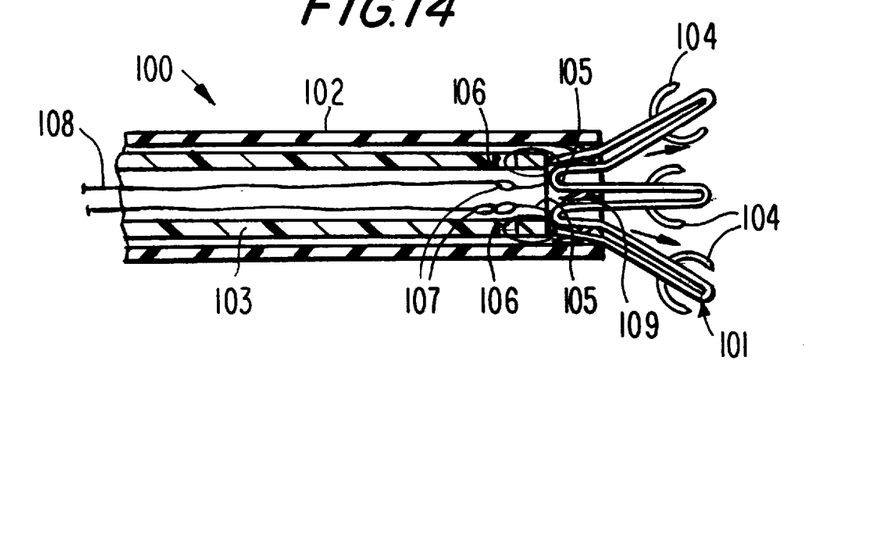
FIG. 14 is an enlarged, cross-sectional view of the distal end of the device depicted in FIG. 12 showing the heart valve of the invention in a partially ejected state.
Figure 15:
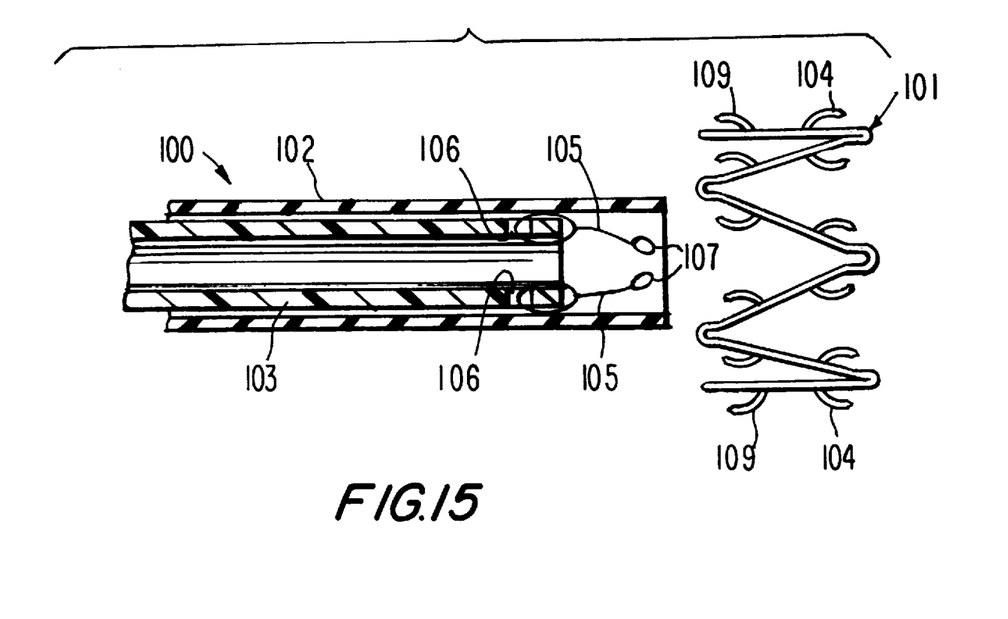
FIG. 15 is an enlarged, cross-sectional view of the distal end of the device depicted in FIG. 12 showing the heart valve fully ejected from the device.

In FIG. 14 there is shown an implanting device 100 of the present invention with a heart valve 101 partially ejected, and FIG. 15 shows the device 100 with the heart valve 101 fully ejected. In FIG. 14 the catheter 102 has been brought to the appropriate site and the guide wire removed proximally. The pusher member 103 has been moved forward longitudinally of the catheter 102 to eject approximately one-half of the heart valve 101 from the distal end of the catheter 102. As seen in the drawing the distal end of the valve 101 is expanded and a slight pull of the entire unit will set the first circle of barbs 104 in the vessel wall. The heart valve 101 is held in place within the delivery catheter by a pair of threads or sutures 105. The sutures are looped through an opening 106 in the pusher member 103 and then passed about a portion of the heart valve 101 as shown. The other end of the suture 105 contains a loop 107. A tension thread 108 is passed through the suture loops and down through the center of the pusher member 103 to the proximal end of the catheter 102. As seen in FIG. 15 the heart valve 101 has been completely ejected from the catheter 102. The tension thread 108 has been removed and the pusher member 103 longitudinally retracted. The looped sutures have been disengaged from the heart valve 101 and the second circle of barbs 109 set in the vessel wall and the valve implanted.

Before the invention herein is used, the patient is studied to determine the architecture of the patient's heart. Useful techniques include fluoroscopy, transesophageal echocardiography, MRI, and angiography. The results of this study will enable the physician to determine the appropriate sized cutting tool and heart valve to employ.

To use Applicant's invention, a guidewire is inserted percutaneously and transluminally using standard vascular or angiography techniques. The distal end of the guidewire is manipulated to extend through and across the defective heart valve. Then a catheter corresponding to catheter 74 is advanced distally through the femoral artery to a point proximal to the defective heart valve, between the origin of the coronary artery and the origin of the right subclavian artery. The position of the distal end of catheter 74 can be monitored by observation of radiopaque markers. Collector member 80 is preferably inflated and occludes the aorta at a point between the origin of the coronary artery and the right subclavian artery. Next, balloon 87 and cutting tool 71 are advanced through catheter 74 so that the cutting tool 71 and uninflated balloon 87 are distal to the defective heart valve. Optionally an additional step, such as balloon dilatation or atherectomy, may be required to provide a passageway through the heart valve.

A catheter is placed into the coronary sinus via a transjugular puncture. This catheter is used for infusion of blood or cardioplegia solution during the portion of the procedure when the aorta is occluded. The absence of valves in the cardiac venous system allows retrograde flow so that there will be an effluence of fluid from the coronary arteries. This flow of fluid is desired to prevent embolization of material into the coronary arteries during the procedure.

Once the cutting tool 71 is in place, the balloon 82 is inflated and flexible shaft 73 is rotated. Once cutting tool 71 has reached the appropriate rotation speed, cutting tool 71 is pulled proximally to remove the defective heart valve. Balloon 87 and cutting tool 71 are spaced apart so that inflated balloon 87 will be stopped by the perimeter, unremoved portion of the defective heart valve, which will signal the physician that the valve has been removed, as well as protect the heart and aorta from damage from the valve removal device. Also, the spacing is such that the cutting tool will not contact collecting member 80. Once it is determined that the defective heart valve has been removed, cutting tool 71 is slowed or stopped altogether and balloon 87 is deflated. Cutting tool 71 and deflated balloon 87 are pulled proximally through catheter 74. Then, a catheter containing an artificial heart valve is inserted and the artificial heart valve is placed as described above.

The valve removal devices and the valve implantation devices of the present invention may be made from any of the materials presently being used commercially to make catheters or angioplasty devices. Examples of such materials include polyvinylchloride, polyethylene, polypropylene, polyurethane, and co-polymers thereof.

In addition, it is within the scope of the invention that the artificial valves described herein can be used to replace or supplement venous valves. Such valves could be delivered percutaneously and transluminally after, or in the absence of, removal of natural venous valves. The artificial valves described above could be used, preferably where the barbs on the outer surface of the stent member are either deleted or reduced, such as one circle of barbs being eliminated. Also, the stent member of a venous valve useful herein could comprise a natural, preserved vein segment with a natural venous valve. One or both ends of the vein segment would comprise self-expandable metal stents that would cause the ends of the segment to remain in position.

Figure 16:
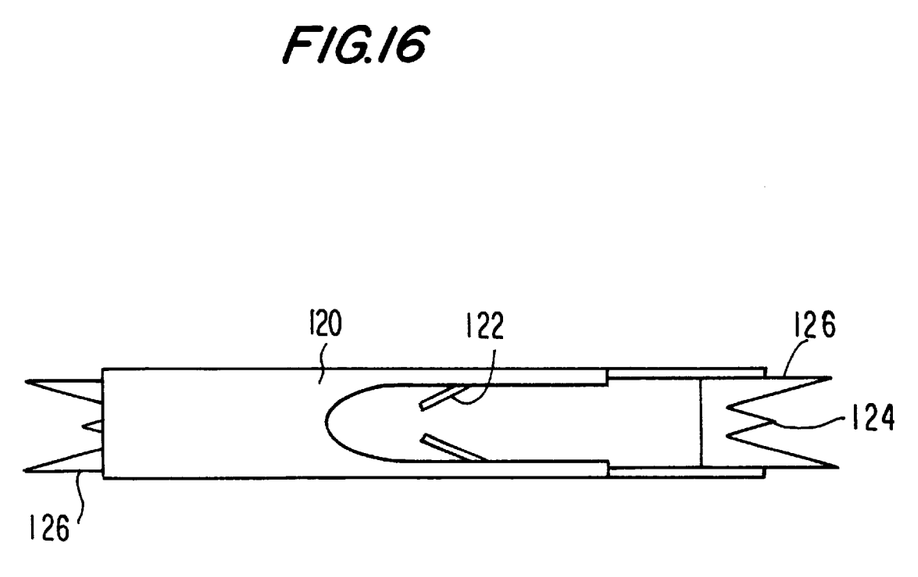
FIG. 16 is a partially cross-sectional view of an artificial heart valve according to the invention useful for venous insufficiency.

As shown in FIG. 16, an artificial venous valve device can comprise a natural vein segment 120 with valve 122, which has a stent 124 at one or both ends of the segment 120. The ends of the segment are secured to the outer surface 126 of stents 124 by suture or other suitable means. Each stent 124 may also contain barbs (not shown), as described above. Such a valve device can be deployed using any one of several possible delivery systems, including the delivery systems described above.

While preferred embodiments of the invention have been illustrated and described, it should be understood that variations will be apparent to those skilled in the art. Accordingly, the invention is not to be limited to the specific embodiments shown and described, but includes all embodiments encompassed within the scope of the following claims.

What is claimed is:

1. An artificial heart valve comprising
   a self-expanding, cylindrical stent member having first and second ends and an outer surface, and
   a valve member comprising one-way valve means arranged within the stent and a cuff portion extending on said outer surface to a point between the first and second ends,
   wherein the cuff portion is configured to position the valve snugly and sealingly at a valve site; and
   wherein the stent member has a plurality of barbs extending from the outer surface of the stent member to engage the natural tissue of the heart to hold the valve in place after implantation.

2. The artificial valve of claim 1, wherein the valve means comprises a plurality of leaflets.

3. The artificial valve of claim 1, wherein the cuff portion extends in the downstream direction.

4. The artificial valve of claim 1, wherein the barbs are disposed in a pair of spaced apart concentric circles.

5. The artificial valve of claim 4, wherein the barbs of one circle are all extending in the same direction and the barbs of the other circle all extending in the opposite direction.

6. The artificial valve of claim 1, wherein the stent member is comprised of a suitable flexible, resilient, biocompatible material.

7. The artificial valve of claim 6, wherein the material is Elgiloy alloy or nitinol.

8. The artificial valve of claim 1, wherein the stent member comprises a closed zig-zag configuration having an endless series of straight sections and a plurality of bends joining said straight sections.

9. The artificial valve of claim 8, wherein the straight sections of said stent member are all substantially the same length.

10. The artificial valve of claim 2 wherein the valve member has three leaflets.

11. The artificial valve of claim 10, wherein the valve member is made of porcine pericardium or a suitable polymeric material.

12. The artificial valve of claim 1, wherein the valve member is attached to the stent member with a plurality of sutures or other attachment means.

13. An artificial heart valve comprising a relatively rigid stent member and a flexible valve means disposed in said stent member, said stent member comprising a wire formed into a closed zig-zag configuration having an endless series of straight sections and a plurality of bends connecting said straight sections, said stent member having a first collapsed cylindrical shape and being self-expandable to a second expanded cylindrical shape, said stent member having a plurality of barbs extending from its outer surface, said valve member comprising a circular portion, said circular portion having a plurality of leaflets extending from the periphery of said circular portion towards the center thereof, said leaflets allowing for flow of blood through the valve in one direction only, the diameter of said circular portion being substantially the same as the inside diameter of said stent member when said stent member is in its expanded cylindrical shape, said valve member having a cuff portion extending from the periphery of said circular portion, said cuff portion being disposed downstream of said valve member and substantially parallel to the cylindrical surface of said stent member and said cuff portion being attached to said stent member with a plurality of sutures.

14. The artificial valve of claim 13, wherein the stent member is a titanium alloy and the valve means has three leaflets and is made of porcine pericardium.

15. The artificial valve of claim 13, wherein the barbs are disposed in a pair of spaced apart concentric circles.

16. The artificial valve of claim 15, wherein the barbs of one circle are all extending in the same direction and the barbs of the other circle all extending in the opposite direction.

17. A method of implanting an artificial heart valve, which method comprises
   providing a transluminal catheter having proximal and distal ends, wherein the distal end carries in a collapsed cylindrical shape a valve comprising a self-expanding, cylindrical stent member having first and second ends and an outer surface, and a valve member comprising one-way valve means arranged within the stent and a cuff portion extending on said outer surface to a point between the first and second ends, wherein the cuff portion is configured to position the valve snugly and sealingly at a valve site; and, wherein the stent member has a plurality of barbs extending from the outer surface of the stent member to engage the natural tissue of the heart to hold the valve in place after implantation,
   positioning the distal end of said catheter at a desired location for placement of said valve,
   moving the leading half of said valve out of the distal end of the catheter to allow the leading half of said valve to expand, and
   retracting the catheter slightly to remove the trailing half of said valve from the hollow end of said catheter to allow the valve to completely expand to place the heart valve in the desired location.

18. The method of claim 17, wherein the valve has a pair of spaced apart concentric circles of barbs extending from the outer surface of said heart valve, one circle of barbs is set when the leading half of the heart valve is moved out of the distal end of said catheter means and the second circle of barbs is set when the trailing half of said heart valve is removed from the distal end of said catheter means.

19. An artificial venous valve comprising
   a tubular valve segment containing venous valve means and having distal ends,
   at least one self-expanding, cylindrical stent member at a valve segment distal end, having first and second ends and an outer surface, and
   a cuff portion extending on the outer surface of each stent to a point between the respective first and second ends,
   wherein each cuff portion is configured to position the respective stent snugly and sealingly at a site; and wherein the stent member has a plurality of barbs extending from the outer surface of the stent member to engage the natural tissue of the site to hold the valve in place after implantation.

20. In an artificial valve for placement in a corporeal duct or vessel wherein said valve comprises a self-expanding stent member and a valve member arranged within the stent member, the improvement wherein a cuff portion extends on the outer surface of said stent member and said cuff member causes said stent member to snugly position itself to the inner surface of the corporeal duct or vessel, wherein the stent member has a plurality of barbs extending from the outer surface of the stent member to engage the natural tissue of the corporeal duct or vessel to hold the valve in place after implantation.

* * * * *